US008236343B2

(12) United States Patent
Jamali

(10) Patent No.: US 8,236,343 B2
(45) Date of Patent: Aug. 7, 2012

(54) METHOD AND APPARATUS FOR IN SITU DRUG DELIVERY DURING DISTRACTION OSTEOGENESIS

(76) Inventor: Amir A. Jamali, Sacramento, CA (US)

( * ) Notice: Subject to any disclaimer, the term of this patent is extended or adjusted under 35 U.S.C. 154(b) by 211 days.

(21) Appl. No.: 12/782,661

(22) Filed: May 18, 2010

(65) Prior Publication Data

US 2010/0292669 A1 Nov. 18, 2010

Related U.S. Application Data

(60) Provisional application No. 61/216,408, filed on May 18, 2009.

(51) Int. Cl.
*A61F 2/00* (2006.01)
(52) U.S. Cl. ........................................ 424/426
(58) Field of Classification Search ............... 604/500
See application file for complete search history.

(56) References Cited

U.S. PATENT DOCUMENTS

| 5,756,127 | A  | * | 5/1998 | Grisoni et al. | 424/489 |
| 6,183,768 | B1 | * | 2/2001 | Harle | 424/423 |
| 2006/0184246 | A1 | * | 8/2006 | Zwirkoski | 623/11.11 |
| 2007/0016163 | A1 | * | 1/2007 | Santini et al. | 604/500 |

* cited by examiner

*Primary Examiner* — Nicholas D Lucchesi
*Assistant Examiner* — Jason Flick
(74) *Attorney, Agent, or Firm* — Craig M. Stainbrook; Stainbrook & Stainbrook, LLP

(57) ABSTRACT

A device and technique for the performance of distraction osteogenesis of bone with controlled drug delivery using a bead chain consisting of two bands and a series of drug delivery capsules placed in a precise manner such that the relative motion of the bone segments brings the wires, pins, or screws into contact with the capsules and divides them. This action sequentially delivers the drug to the distraction zone throughout the distraction osteogenesis process.

9 Claims, 6 Drawing Sheets

METHOD AND APPARATUS FOR IN SITU DRUG DELIVERY DURING DISTRACTION OSTEOGENESIS

CROSS REFERENCES TO RELATED APPLICATIONS

The present application claims the benefit of U.S. Provisional Patent Application Ser. No. 61/216,408, filed May 18, 2010 (May 18, 2009).

STATEMENT REGARDING FEDERALLY SPONSORED RESEARCH OR DEVELOPMENT

Not applicable.

NAMES OR PARTIES TO A JOINT RESEARCH AGREEMENT

Not applicable.

INCORPORATION-BY-REFERENCE OF MATERIAL SUBMITTED ON A COMPACT DISC

Not applicable.

SEQUENCE LISTING

Not applicable.

BACKGROUND OF THE INVENTION

1. Field of the Invention

The invention relates generally to drug delivery systems, and more specifically to a method and apparatus for in situ drug delivery for use in distraction osteogenesis.

2. Background Discussion

Distraction osteogenesis (DO) is an important technique for bone restoration. The procedure was pioneered by Dr. Gavril Ilizarov. The fundamental technical principle underlying the procedure is that by using a corticotomy to cut the cortex of a bone while maintaining the periosteal cover, an internal or external fixation device may be used to gradually separate the ends of the bone sections during the distraction phase of the process so as to lengthen the bone healing callus. In effect, it is a method of stretching existing bone by fostering growth in the gap between the separated bone sections. When the desired amount of growth or increased bone length or shape is achieved, the bones are allowed to continue healing during a consolidation phase. However, if the speed of the distraction is excessively fast, a nonunion can occur. Conversely, if the speed of distraction is too slow, the corticotomy can heal requiring a secondary corticotomy. Clinically, most fixators are distracted at a specific rate to ensure proper bone lengthening while preventing premature fusion. Once the desired degree of lengthening is achieved, most experts recommend a consolidation period of at least twice as long as the lengthening period.

Distraction osteogenesis can be used for a variety of indications including congenital deformities, traumatic injuries, infection, and tumors. Traditionally, distraction osteogenesis of the extremities has been performed with a ring external fixator with fine wires or half pins in the long bones. However, the indications for this procedure have expanded, particularly to include procedures in craniofacial surgery. A number of advances have been achieved in this area including the use of submergible distractors that can be placed under the skin, such as the implantable plate for distracting mandibular bone segments as, disclosed by Chin, U.S. Pat. No. 5,810,812.

Another recent innovation involves the use of plates attached to the bone for distraction osteogenesis, as disclosed by Elsalanty, WO 2005/086920. Others have described the use of bioabsorbable fixation foot plates connected with a telescoping rod for use in distraction osteogenesis, such as the apparatus described by Buchbinder, U.S. Pat. No. 6,293,947 B1.

Additional refinements of telescopic distraction osteogenesis systems have been proposed by Kourtis, EP 1 016 381 A1, and by Walker, U.S. Pat. No. 5,902,304.

One of the major obstacles to widespread use of distraction osteogenesis, particularly in the long bones, is the extensive period of time required for consolidation of the regenerated bone. The best strategy currently known for addressing this problem has been the use of drug delivery to the site of the distraction. A number of therapeutic agents and delivery methods have been developed to achieve this goal. Pharmacological agents employed to this end include, among others, growth factors and morphogens. The most widely accepted agent is bone morphogenic protein (BMP), which is routinely used in spinal fusion as well as in certain open extremity fractures.

Cheung et al studied the effect of increased distraction rate in a New Zealand White Rabbit mandibular distraction model with the addition of recombinant human BMP (rhBMP-2). Kim et al. have shown that in a dog model of mandibular distraction osteogenesis, BMP leads to substantially more bone than control when implanted at the end of the distraction period. Both of these studies employed a one-time delivery of BMP, and thus shed no light on whether additional delivery of BMP would affect the outcome.

Another strategy published by Ashinoff et al, involves the use of an adenovirus containing the gene for BMP-2. This virus was implanted into the distraction zone in a rat model of mandibular distraction osteogenesis at the end of the distraction period. The researchers found a significantly higher volume of bone in this group than in the control group. The advantage of this technique is the potential for longer drug exposure of the distraction zone resulting from the viral vector. At both 2 and 4 weeks of the consolidation period, they noted increased bone volumes in the BMP group. However at the 8 week mark, there was no difference in the mechanical strength between the BMP and control groups.

Angiogenic factors such as vascular endothelial growth factor (VEGF) provide yet another strategy to enhance bone regeneration speed and thereby to minimize the treatment duration in DO. Hu et al have shown that endogenous levels of VEGF are upregulated during the distraction process. Casap et al analyzed the effect of VEGF in a model of periosteal distraction osteogenesis whereby the periosteum is distracted to form new bone. In a rabbit model, they compared the effect of daily injections of VEGF for four days during the distraction process to control periosteal distraction. They found a statistically significant increase in bone volume using micro-computed tomography analysis in the VEGF group.

In spite of these remarkable results, the ability to regularly and repeatedly deliver drugs to the site of distraction osteogenesis remains an ongoing challenge. Grayson et al. have developed a device for drug delivery during DO using a cannulated pin system. (see Grayson, B. H., et al, *Development of a device for the delivery of agents to bone during distraction osteogenesis*, J Craniofacial Surg. 2001: 12(1):19-25.) India ink was injected into the pins in a canine mandibular DO model. The ink spread radially outward from the pins on visual examination and could be found within the regenerated bone under histological (microscopic) evaluation.

Konas, WO 2008/030201 A1, discloses a method for drug delivery with a internally mounted piston distractor. The distractor releases drug agents through the movements of the distractor and the rotation of a rod, which are transmitted to a piston inserted in a drug container. This leads to an incremental drug release during the distraction process.

However, there are still several challenges present in delivering constant amounts of drug at the site of bone distraction. Strategies to address this problem include the use of drug eluting pins, osmotic pumps, and multiple injections into the site. The present invention provides a device and method for applying any drug to the distraction site mechanically.

The foregoing patents and other publications reflect the current state of the art of which the present inventor is aware. Reference to, and discussion of, these publications is intended to aid in discharging Applicant's acknowledged duty of candor in disclosing information that may be relevant to the examination of claims to the present invention. However, none of the above-indicated publications disclose, teach, suggest, show, or otherwise render obvious, either singly or when considered in combination, the invention described and claimed herein.

BRIEF SUMMARY OF THE INVENTION

The present invention differs from the apparatus shown by Konas in that the drug release does not depend on any function of the distractor itself. Rather, a constant flow of fresh pharmacological agents are released at the distraction site through the gradual motion of wires and pins relative to one another. The wires and pins sequentially divide drug containing capsules in a drug delivery chain.

It is therefore a first and principal object of the present invention to provide a method and device for the delivery of various drugs to the site of distraction osteogenesis for a variety of purposes including accelerated bone regenerate consolidation, prevention of infection and tumors, as well as other purposes.

It is another object of the present invention to provide a method and device for the delivering drugs to a distraction osteogenesis site for any location and type of distraction osteogenesis.

To achieve these objects, the present invention is a drug delivery apparatus for in situ drug delivery to a distraction osteogenesis site comprising a bead chain having two bands and multiple intervening drug delivery capsules in series which connect the two bands at each capsule. The bands are fixed on the near side of the bone sections to be distracted by any of a variety of fixation devices, such as screws, pins, anchors, etc. The two bands then pass across the distraction zone (corticotomy) and pass around the first wire, pin, or screw used for fixation of the distractor the far side of the corticotomy. The bead chain is positioned such that the first drug delivery capsule is positioned down the chain. As the distraction osteogenesis is carried out, the wire, pin, or screw used on the far side of the corticotomy is translated slowly down the far side of the chain which is fixed rigidly at the near side of the distraction zone. As this occurs, the wire, pin, or screw eventually comes into contact with the first drug delivery capsule. When sufficient tension is applied to the capsule by the wire, pin, or screw, the drug delivery capsule divides or breaks, thereby releasing the contents of the capsule into the immediately surrounding space, tissues, and local microenvironment. In succession, the individual capsules in the chain of drug delivery capsules are encountered and broken during the entire distraction process, leading to a consistent release of the drug into the distraction zone throughout the process. Additionally, multiple bead chains can be applied in different positions around the bone in order to release the drug on all sides of the distraction zone.

Other novel features characteristic of the invention, as to structure, composition, organization, and method of operation, together with further objects and advantages thereof will be better understood from the following description, considered in connection with the accompanying drawings, in which preferred embodiments of the invention are illustrated by way of example. Those skilled in the art will appreciate that the conception, upon which this disclosure is based may readily be used as a basis for designing other structures, methods, and systems for carrying out the several purposes of the present invention. The claims should be understood to include such equivalent constructions as far as they do not depart from the spirit and scope of the present invention.

BRIEF DESCRIPTION OF THE SEVERAL VIEWS OF THE DRAWINGS

The invention will be better understood and objects other than those set forth above will become apparent when consideration is given to the following detailed description thereof. Such description makes reference to the annexed drawings wherein.

DETAILED DESCRIPTION OF THE INVENTION

Figure 1:
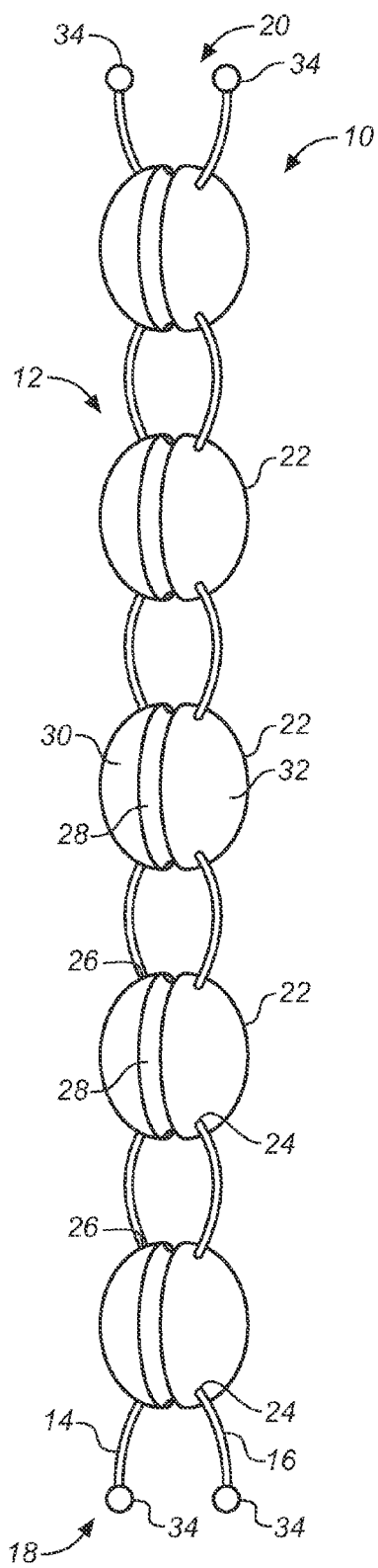
FIG. 1 is a schematic view showing the essential structural and functional elements of the present invention, including two bands connecting a series of drug delivery capsules in a generally linear array.

Referring first to FIGS. 1 through 5, wherein like reference numerals refer to like components in the various views, there is illustrated a new and improved drug delivery apparatus for use in distraction osteogenesis, generally denominated 10 herein. The inventive apparatus can be applied to distraction osteogenesis or periosteal distraction osteogenesis at any site in the skeleton.

In a first preferred embodiment of the invention, the invention can be used to treat a long bone defect secondary to a tumor. FIG. 1 is a schematic illustration showing the essential structural and functional components of the invention. Here is it is seen that the invention comprises a bead chain 12 that includes at least one or two bioabsorbable bands, wires, strings, cords, or threads 14, 16, each having a first end 18 and a second end 20. If a single band is employed, it is continuous or integrally connected at one end, bent to form a return side, and open or disconnected at the other end. Accordingly, whether one or two bands are employed, the bands form side-by-side generally parallel segments of material having substantially the same length.

The invention next includes a plurality of hollow drug delivery capsules 22 disposed along the length of the band(s). Each drug delivery capsule includes first and second through holes 24, 26, into which the bands are inserted and through which they are passed. As noted in the preceding paragraph, there are at least one or two bands. This should be taken to mean that in an alternative embodiment, a plurality of bands may be employed, a pair disposed between each adjoining set of drug delivery capsules.

The drug delivery capsules may be any of a number of suitable shapes, though a generally spherical shape is well suited to the use. Each capsule includes an interior volume into which a pharmacological agent is pre-injected. In the preferred embodiment, the capsules are each notched with a circumferential groove 28, which divides the capsules generally into first and second portions or halves 30, 32. The groove is straddled by the band(s) 14, such that each portion of the capsule is disposed on a band. The groove constitutes a deliberate structural weakening, such as a partial break, etch, stamped edge, and the like, formed in the capsule wall and it is considerably more prone to failure and breaking than the other portions of the capsule. As will be appreciated, the band length can be adjusted and the spacing between the capsules adjusted according to the needs of the specific application. Indeed, the bands can be continuous lengths disposed through the capsules, or can be discontinuous and disposed only between each adjoining pair of capsules along the chain. Furthermore, the contents of the drug delivery capsules can be adjusted based on the specific location along the bead chain and the desired biological goal at that time in the distraction process. The drug delivery capsules are preferably fabricated from bioabsorbable polymers including, but not limited to, polylactic acids or polyglycolic acids, collagens, hyaluronic acids, or any combination thereof. The drugs contained in the capsules will generally consist of various morphogens and growth factors such as, but not limited to, transforming growth factor, bone morphogenic protein, insulin-like growth factor, vascular endothelial growth factor, as well as various antibiotic, antineoplastic, or anti-resorptive agents.

If desired, two foot plates or attachment rings 34 can be affixed at either the first or second ends of the bands for fixation to the bone on the near side and far sides of the distraction zone. If a plurality of bands are employed, the terminal bands (i.e., those extending from the end drug delivery capsules) are provided with attachment rings or other attachment apparatus.

Figure 2:
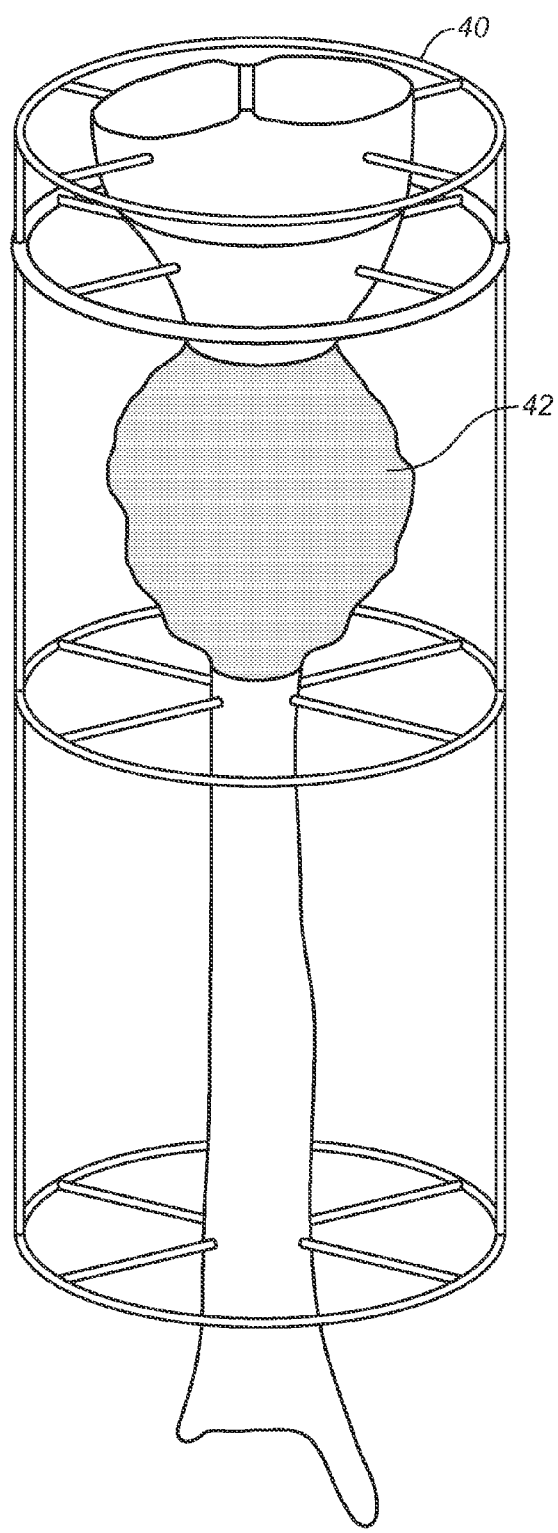
FIG. 2 is a schematic front perspective view of a bone tumor in the tibia prior to resection and after application of a ring external fixator.
Figure 3:
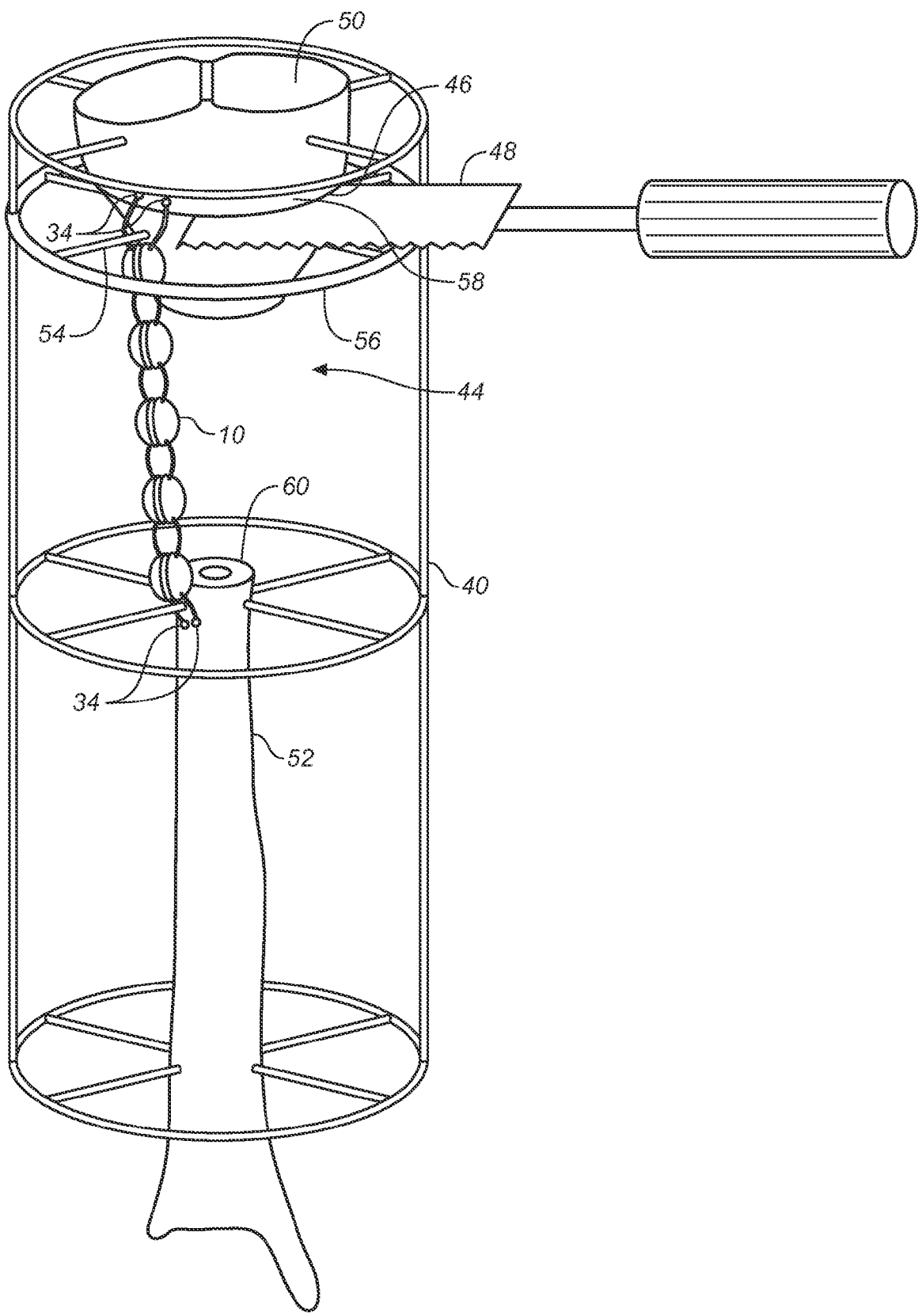
FIG. 3 is a schematic front perspective view of the tibia after resection of the tumor using a bone saw and application of the bead chain across the bone defect, and demonstrating the technique of bone transport for spanning the bone defect.

Referring next to FIG. 2, there is shown the placement of a ring external fixator 40 prior to resection of a tibial tumor 42. After resection, and referring now to FIG. 3, a resulting bone gap 44 remains. In this case, bone transport and distraction osteogenesis is used to address the defect.

The methods to perform this procedure are well known to those skilled in the art of bone surgery. Summarily, the procedure consists of a corticotomy 46 using a bone saw 48 on the upper part of the tibia 50. The intervening bone segment is transported along a ring external fixator 40 down the leg to dock onto the residual distal tibia 52. The corticotomy is performed just above the first pin or wire 54 of the transport ring 56. The bead chain 10 is then attached to the near side 58 of the distraction site or corticomy using the attachment rings 34 in such a way that each band passes on one side of the first pin or wire 54 and such that the bands then connect at the first drug delivery capsule. The bead chain is attached to the far side 60 of the distraction site on the residual distal tibia using the same means.

Figure 4:
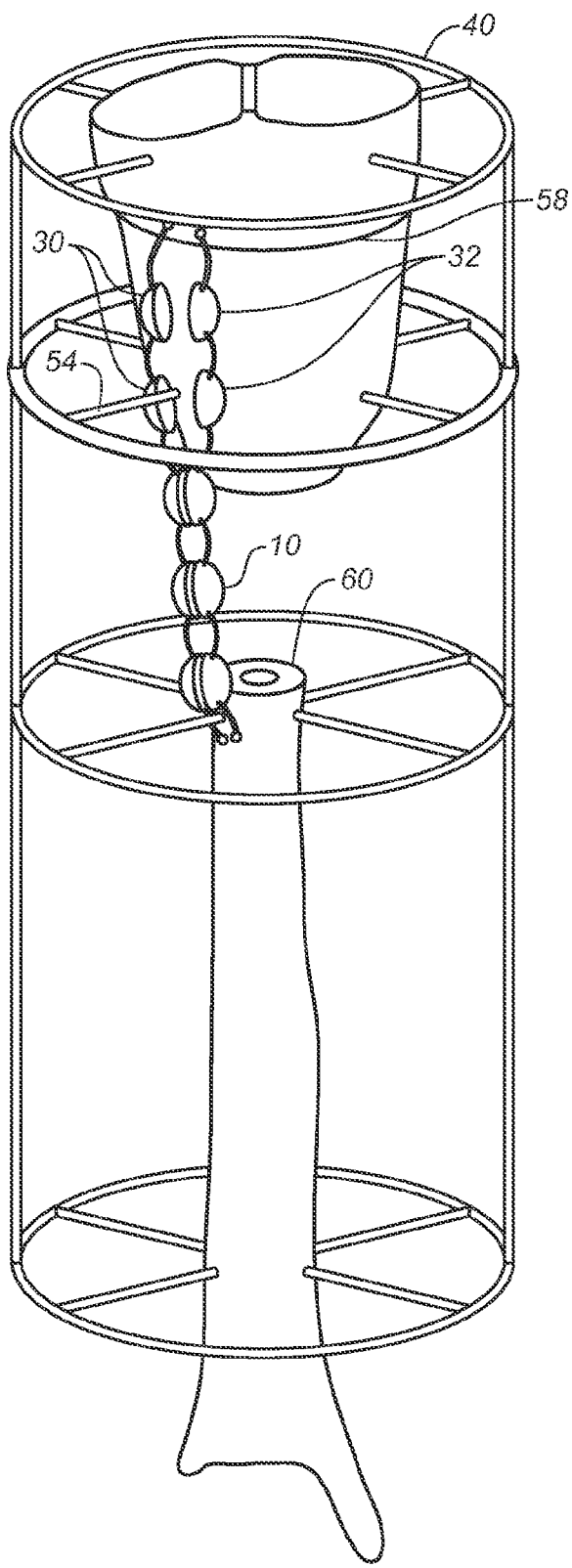
FIG. 4 is a schematic front perspective view of the tibia during the process of bone transport and showing the division of the drug delivery capsules by the fixator wires.

As shown in FIG. 4, during the distraction process, the first pin or wire 54 engages the first drug delivery capsule at its upper portion and cleanly divides the capsule along the circumferential groove, thereby releasing the previously encapsulated drug into the local environment. As the distraction continues, FIG. 5, capsule after capsule is split in succession to release a controlled volume of drug at the desired site until the end of the distraction period.

Figure 5:
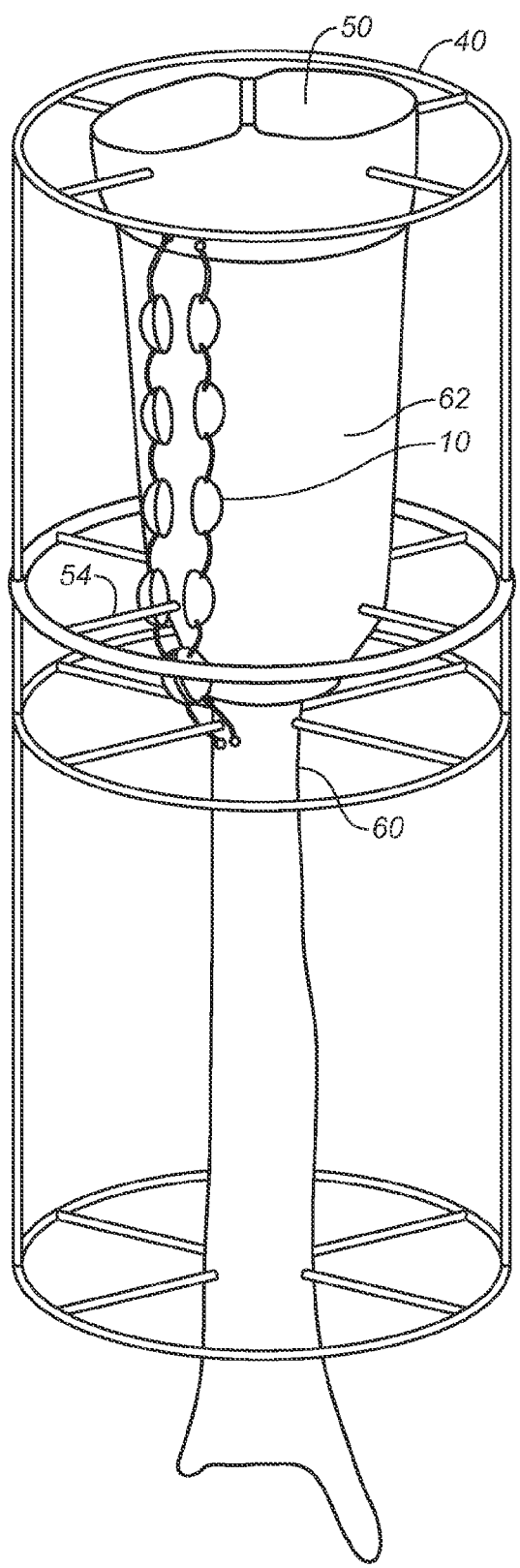
FIG. 5 is a schematic front perspective view of the tibia after docking of the bone transport on the distal tibia and after division of multiple drug delivery capsules.

As shown in FIG. 5, the new bone regenerate 62 will ultimately span the tumor defect as the regenerated bone contacts and heals to the residual tibia 60.

Figure 6:
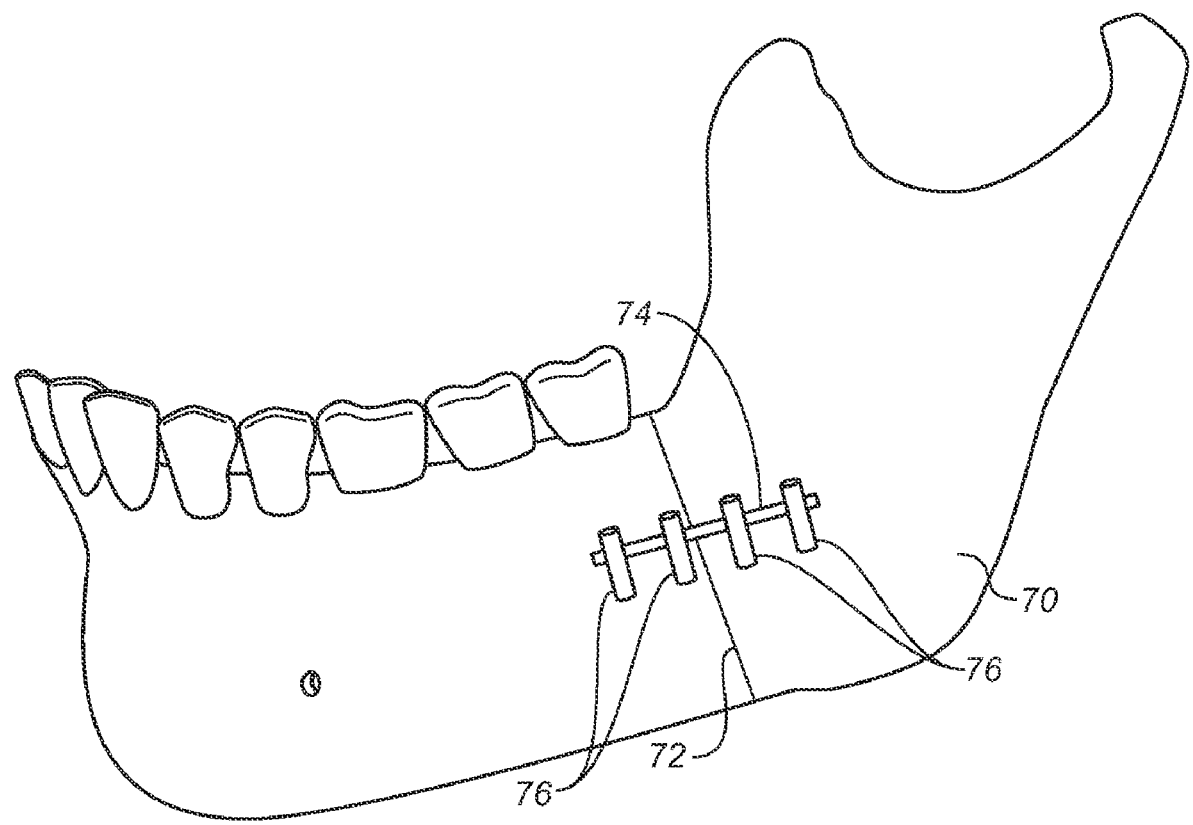
FIG. 6 is a schematic side view in elevation of a mandible prior to distraction osteogenesis for lengthening after performance of a corticotomy and application of an external fixator.

In another preferred embodiment, the inventive apparatus is adapted for use in craniofacial distraction osteogenesis, such as in distraction osteogenesis of the mandible. In FIG. 6, a mandible 70 is shown prior to distraction osteogenesis. The specific devices used in distraction osteogenesis of the mandible are variable but all include a method of spanning the corticotomy to apply controlled and consistent distraction, whether through the use of pins, screws, or plates. In this case, a corticotomy 72 is performed with a spanning telescopic bar 74 and two pins 76 on either side.

Figure 7:
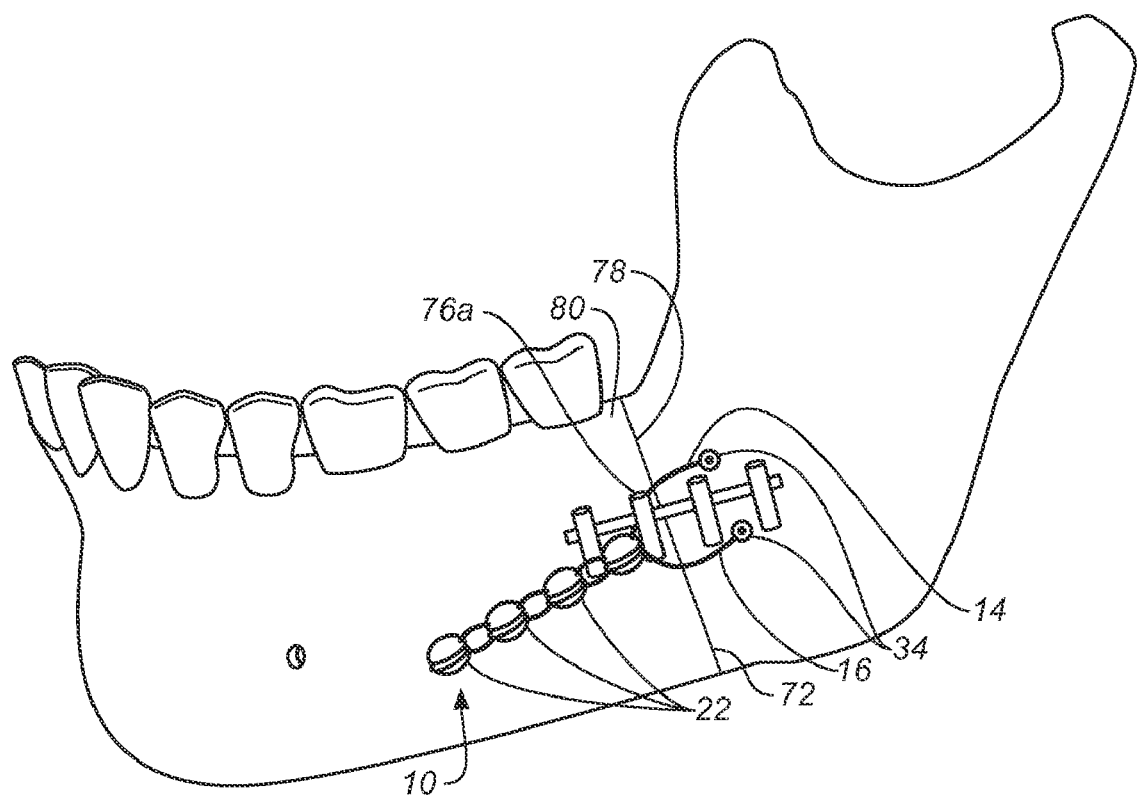
FIG. 7 is a schematic side view of the mandible after application of the bead chain comprising two bands and multiple drug delivery capsules.

In FIG. 7, a bead chain 10 is applied to the mandible on the near side 78 of the distraction site using two foot plates 34 attached to bands 16 crossing the corticotomy 72 and passing on either side of the first distraction pin 72a on the far side 80 of the corticotomy. Multiple drug delivery capsules 22 attached to the bands are then placed along the mandible more distally.

Figure 8:
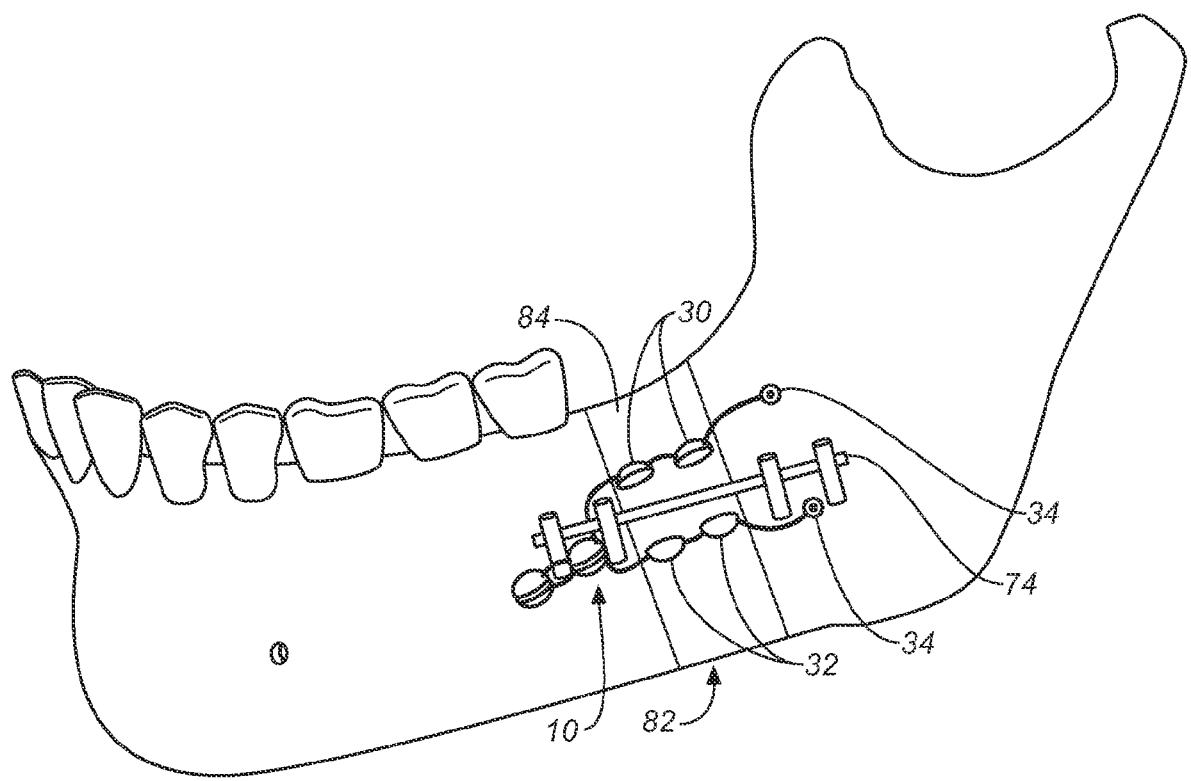
FIG. 8 is a schematic side view of the mandible at the end of the distraction process after division of the multiple drug delivery capsules by the pins in the distractor.

As seen in FIG. 8, the distraction is performed by lengthening of the telescopic bar 74, increasing the distance between the pins on either side of the distraction site 82. This brings the pins on the far side of the distraction site into contact with the first of the drug delivery capsules and ultimately divides it into two sections 30, 32, thereby releasing its contents into the local environment. The same process is performed sequentially on all the capsules in the bead chain until the end of the distraction process. Again, the new bone regenerate 84 will span the previous defect as the regenerated bone contacts and heals to bone end or border on the distal portion of the mandible.

As will be readily appreciated from the foregoing, in its most essential aspect, the present invention is an internally placed drug delivery system for distraction osteogenesis with the novel capability of releasing drugs at the site of distraction and consolidation by the placement of a bead chain and mechanical disruption of the beads by the displacement of pins, wires, or distraction plates relative to one another.

The above disclosure is sufficient to enable one of ordinary skill in the art to practice the invention. The description also provides the best mode of practicing the invention presently contemplated by the inventor. However, while there is provided herein a full and complete disclosure of the preferred embodiments of this invention, the written description and the drawings do not limit the invention to the exact construction, dimensional relationships, and operation shown and described. Various modifications, alternative constructions, changes and equivalents will readily occur to those skilled in the art and may be employed, as suitable, without departing from the true spirit and scope of the invention.

What is claimed as invention is:

1. A drug delivery apparatus for in situ drug delivery to a distraction osteogenesis site, comprising: at least one band configured into first and second longitudinally oriented and spaced apart band segments having generally the same length; a plurality of drug delivery capsules having an interior volume for containing a pharmacological agent, said drug delivery capsules having first and second portions, each of said first and second portions being disposed on or connected to one of said band segments, the other of said portions being connected to the other of said band segments, such that said drug delivery capsules are disposed on said band segments so as to form a generally linear array, and such that at least two band segments are disposed between any given adjoining pair of said drug delivery capsules; connection apparatus for connecting said band segments to bone; and a pharmacological agent disposed inside each of said drug delivery capsules.

2. The apparatus of claim 1, wherein said bands are bioabsorbable.

3. The apparatus of claim 1, wherein said bands are longitudinally disposed and connect said drug delivery capsules in series.

4. The apparatus of claim 1, wherein each of said first and second portions of said drug delivery capsules includes a through hole through which one of said band segments is passed.

5. The apparatus of claim 1, wherein said first and second portions of said drug delivery capsules are defined by a groove.

6. The apparatus of claim 1, wherein said drug delivery capsules are disposed on only one band with a bend so as to form said first and second band segments.

7. The apparatus of claim 1, wherein said connection apparatus comprises attachment rings.

8. The apparatus of claim 1, further including a fixator pin, wherein said band segments each include a first end and a second end and connection apparatus disposed at each of said first and second ends, such that by connecting said first ends to the near side of a corticotomy and said second ends to the far side of a corticotomy, a corticotomy fixator pin disposed between said band segments above said drug delivery capsule nearest said first ends of said band segments will progressively migrate from said first ends toward said second ends during bone distraction and will thereby mechanically disrupt and break said drug delivery capsules to release said pharmacological agents.

9. A drug delivery system for use in a distraction osteogenesis procedures for releasing drugs at the site of distraction and bone regenerate consolidation, comprising a side-by-side elongate cords having first and second ends, a plurality of drug delivery capsules disposed along the length of said cords such that at least two of said cords are disposed between any two adjoining of said drug delivery capsules, and fixation means for anchoring said first and second ends of said elongate cords to the near and far side of a distraction site, wherein a fixator element attached to the near side of a distraction site and between said cords will be translated between and along the length of the cords so as to mechanically break open the drug delivery capsules to release any contents contained therein.

* * * * *